United States Patent [19]
Anderson et al.

[11] Patent Number: 5,645,062
[45] Date of Patent: Jul. 8, 1997

[54] BIOMEDICAL ELECTRODE DEVICE

[76] Inventors: John McCune Anderson, 16 Torgrange, Holywood, County Down, BT18 ONG, Northern Ireland; Eric Thomas McAdams, Ormsdale, 52 Cable Road, Whitehead, County Antrim, Northern Ireland BT38 9 PZ; Dermot Frances McCafferty, 50 Cesaeldone Rise, Belfast, BT6 9RA, Northern Ireland; James Andrew McLaughlin, 9 Hampton Gardens, Hampton Court Village, Belfast BT7 3DF, Northern Ireland; Aaron David Woolfson, 6 Malone Meadows, Belfast BT9 5BG, Northern Ireland, all of United Kingdom

[21] Appl. No.: 196,465

[22] Filed: Feb. 15, 1994

[30] Foreign Application Priority Data

Feb. 15, 1993 [IE] Ireland ............................ 930103

[51] Int. Cl.⁶ ............................................. A61B 5/0408
[52] U.S. Cl. ........................................ 128/640; 128/642
[58] Field of Search ........................ 128/640, 643, 128/639, 641, 642; 607/149, 152

[56] References Cited

U.S. PATENT DOCUMENTS

| | | | |
|---|---|---|---|
| 4,539,996 | 9/1985 | Engel | 128/640 |
| 4,543,958 | 10/1985 | Cartmell | 128/640 |
| 4,699,146 | 10/1987 | Sieverding | 128/640 |
| 4,766,005 | 8/1988 | Montgomery | 427/323 |
| 4,848,353 | 7/1989 | Engel | 128/640 |
| 4,860,754 | 8/1989 | Sharik et al. | 607/149 |
| 4,989,607 | 2/1991 | Keusch et al. | 607/152 |
| 5,003,978 | 4/1991 | Dunseath, Jr. | 128/640 |
| 5,143,071 | 9/1992 | Keush et al. | 128/640 |
| 5,178,143 | 1/1993 | Kwak et al. | 128/639 |

FOREIGN PATENT DOCUMENTS

| | | |
|---|---|---|
| 0085327 | 8/1983 | European Pat. Off. . |
| 0255241 | 2/1988 | European Pat. Off. . |
| 0409067 | 1/1991 | European Pat. Off. . |
| 3816190 | 8/1989 | Germany . |
| 1520351 | 8/1978 | United Kingdom . |
| 2034184 | 6/1980 | United Kingdom . |
| 1574363 | 9/1980 | United Kingdom . |

OTHER PUBLICATIONS

Comprehensive Maternity Nursing, Nursing Process and the Childbearing Family, second edition, J.B. Lippincott Company, pp. 676–687.

Handbook of Pressure–Sensitive Adhesive Technology, Donatas Satas, Van Nostrand Reinhold Company, New York, 1982, pp. 1–25.

*Primary Examiner*—Lee S. Cohen
*Attorney, Agent, or Firm*—Sughrue, Mion, Zinn, Macpeak & Seas

[57] ABSTRACT

A biomedical electrode device comprises an electrically insulating substrate carrying an electrode. The electrode is coated with a moisture-activated electrically conductive bioadhesive layer having an adhesion of between 50 and 500 g/cm² and a water content of less than 25% w/w.

13 Claims, 9 Drawing Sheets

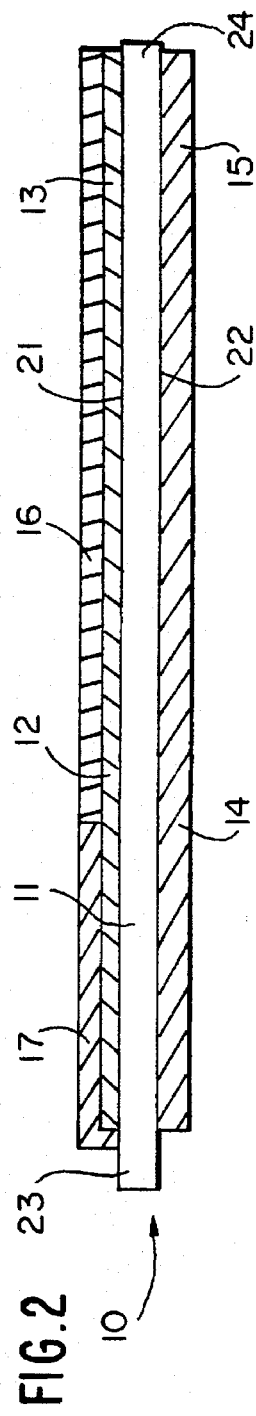
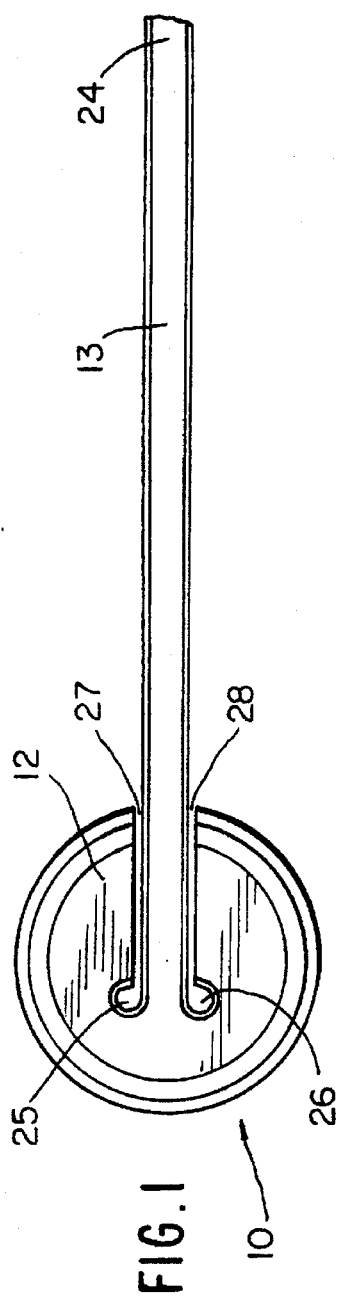
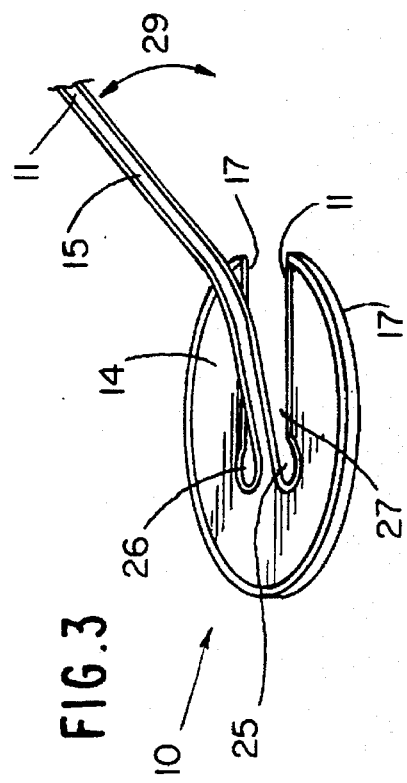

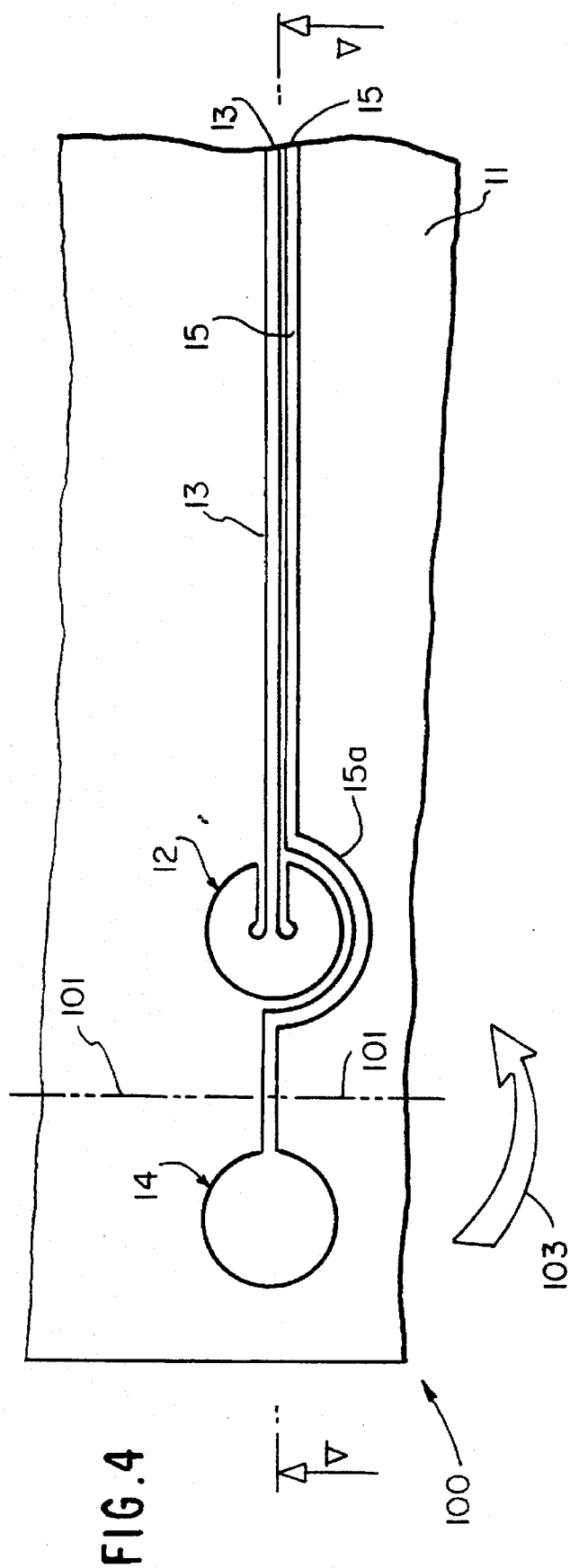
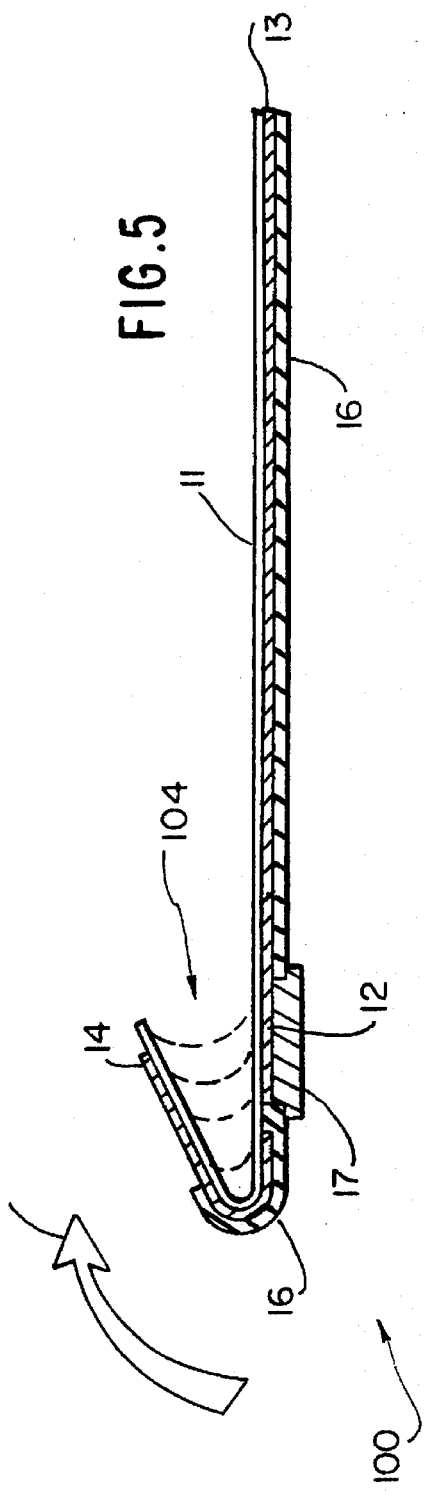

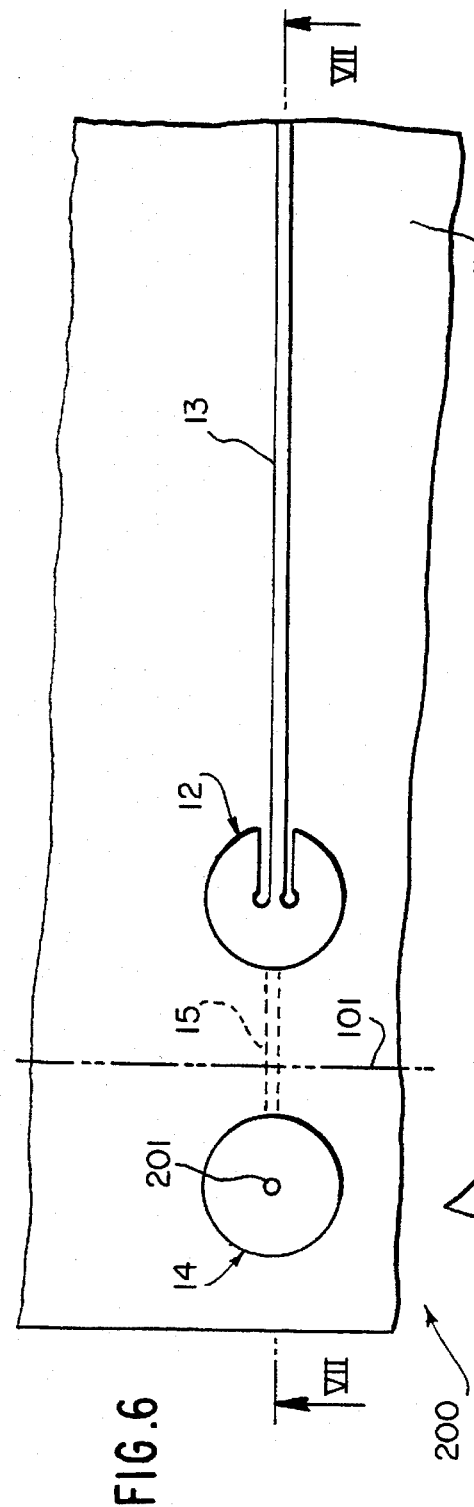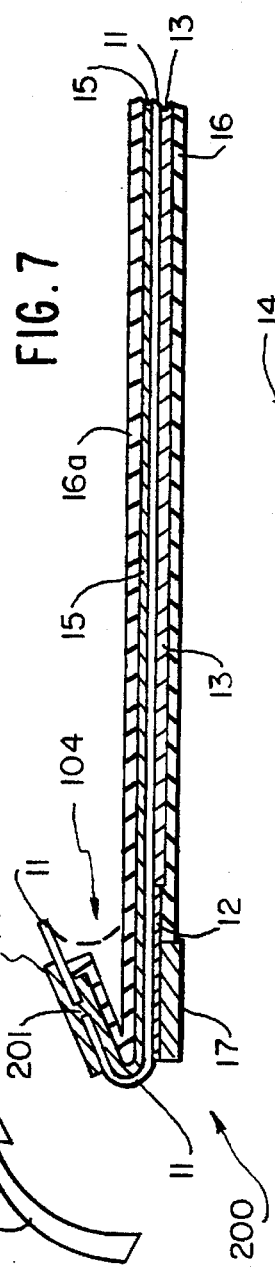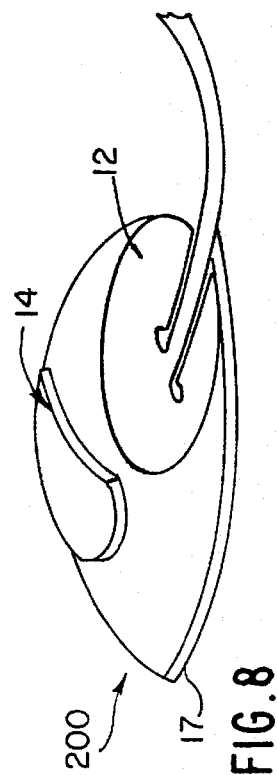

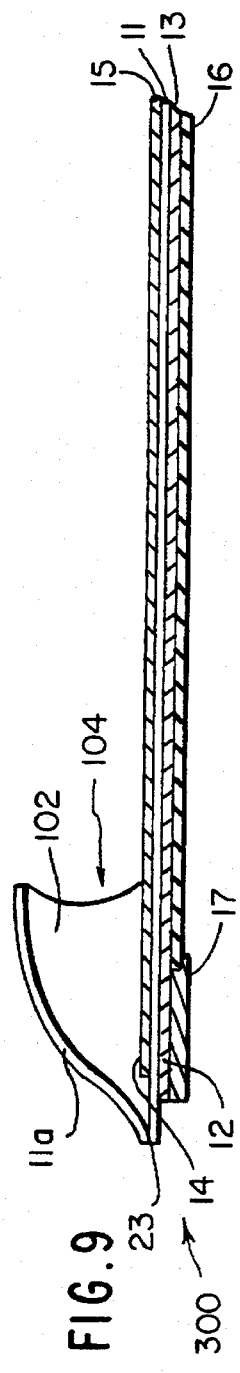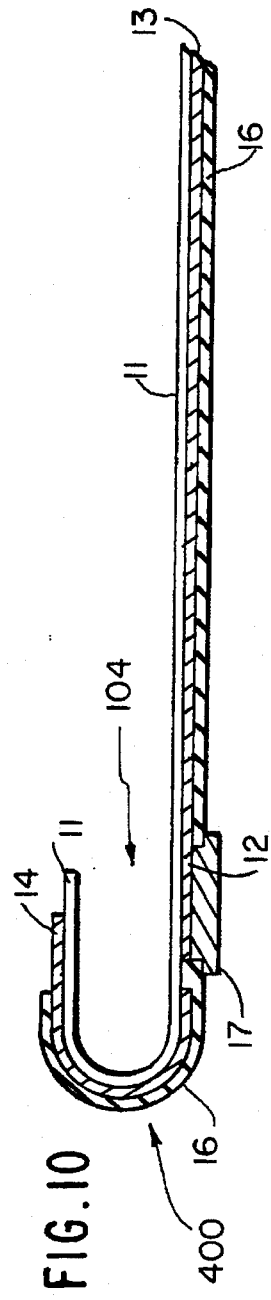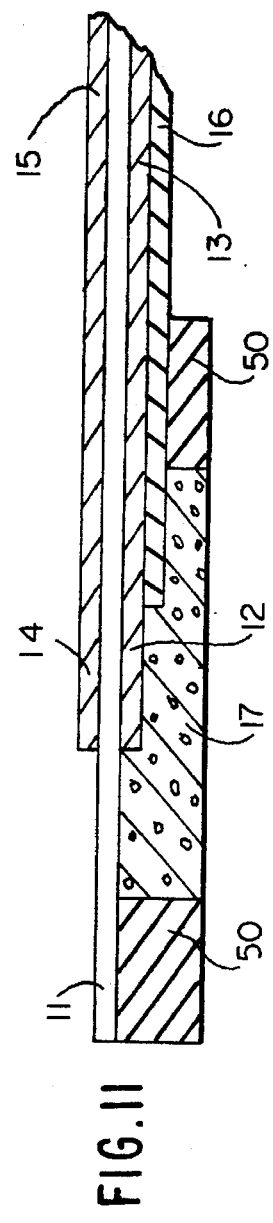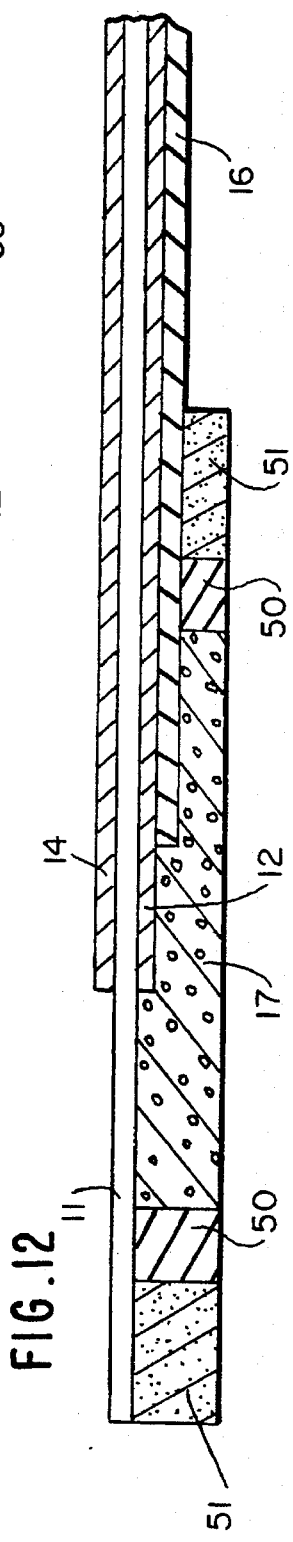

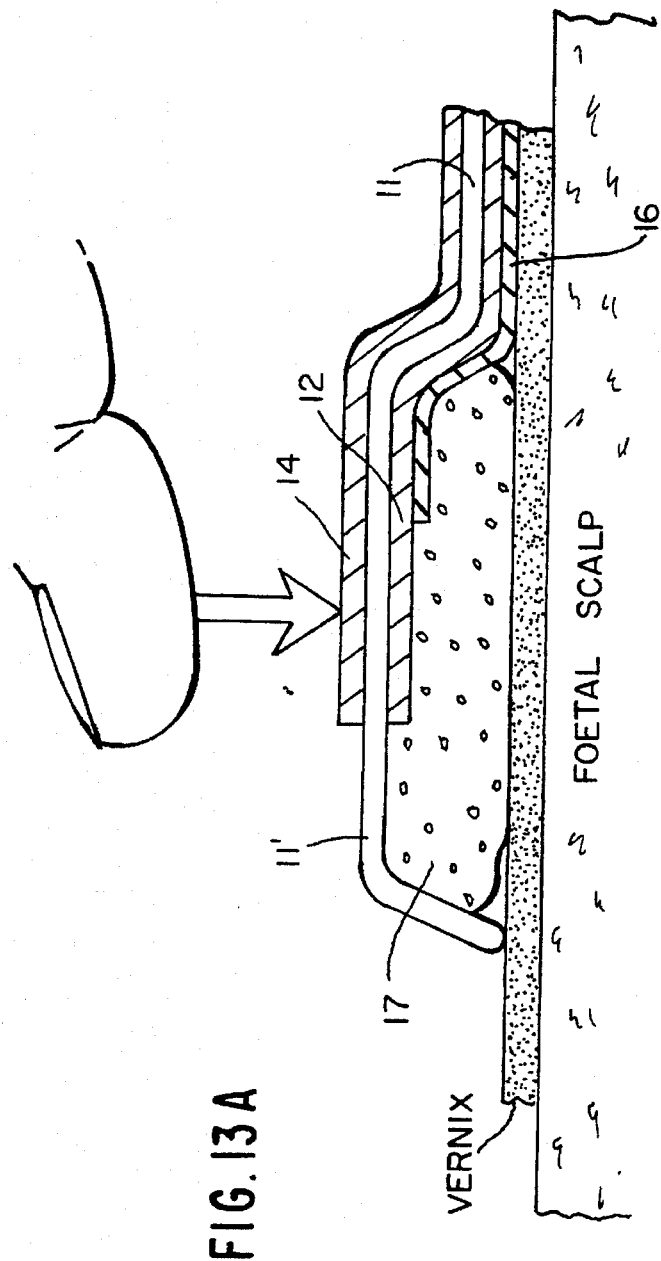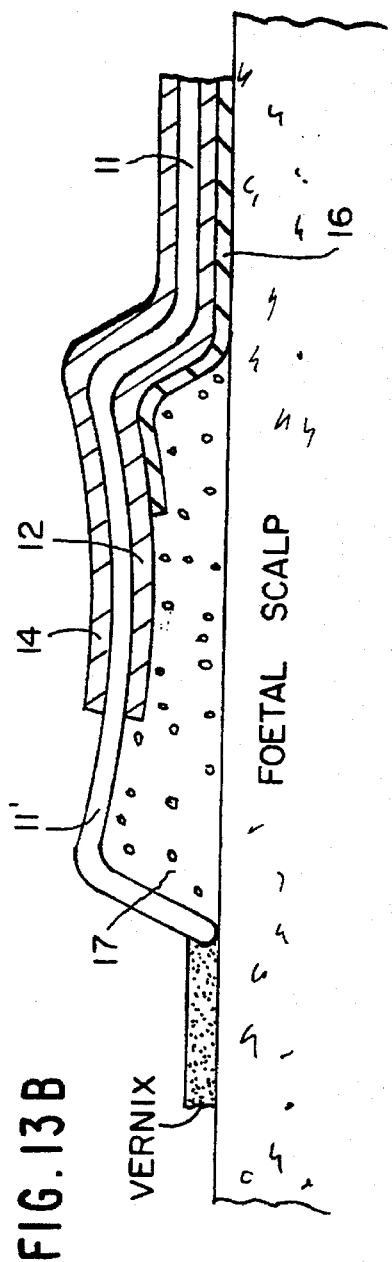

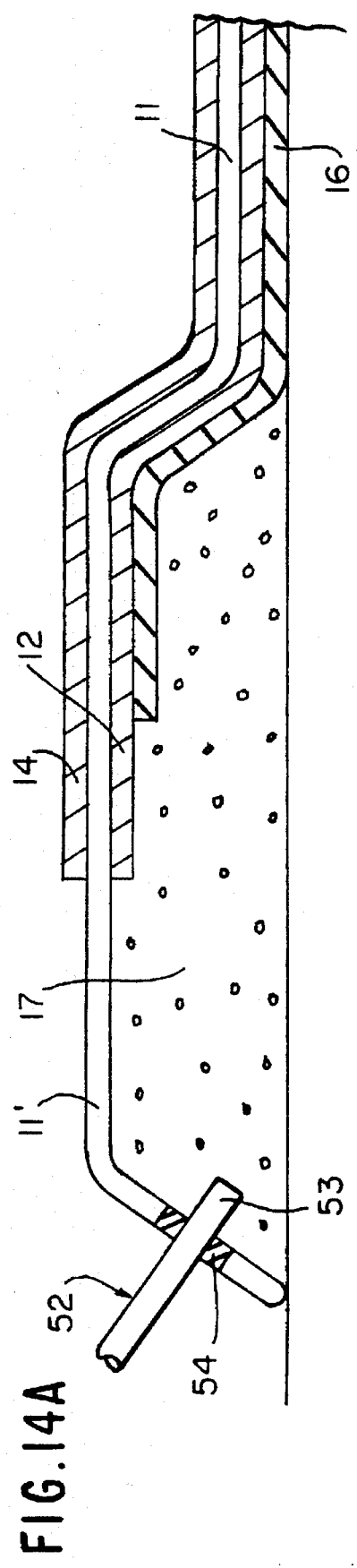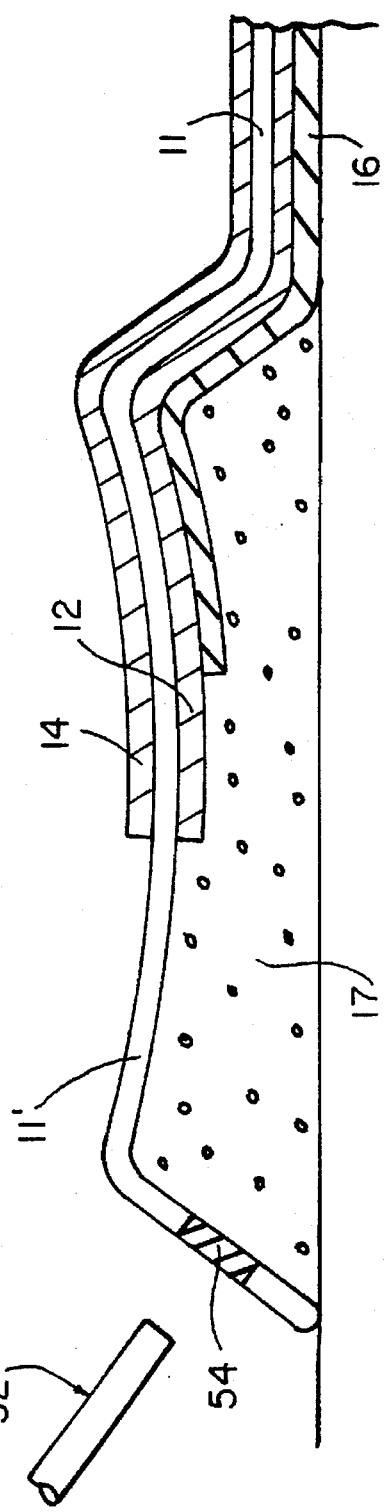

BIOMEDICAL ELECTRODE DEVICE

BACKGROUND OF THE INVENTION

This invention relates to a biomedical electrode. In particular, it relates to a biomedical electrode for use in the prolonged monitoring of a bio-electrical signal in a wet environment. In the preferred embodiments it relates to a biomedical electrode for use in the continuous monitoring of a foetal heart rate during labour.

Biomedical electrodes for external monitoring of electrical signals in humans are known in the art. Adhesives suitable for securing such electrodes to human skin are also known in the art. These adhesives are electrically conductive creams, pastes or gels applied directly to dry skin, thus forming an interface with the electrode. The Patent literature discloses several electrode designs incorporating the conducting adhesive as a coating on the electrode surface (for example, U.S. Pat. Nos. 4,674,512, 4,391,278, 4,125,110 and 4, 391,278). Removal of a release paper or liner allows direct attachment of the electrode to dry skin by application of light pressure. Thus, this type of design requires a pressure-sensitive adhesive. Pressure-sensitive adhesives may be produced conventionally by compounding an elastomer with a tackifying resin, or alternatively by using polymers which are inherently pressure-sensitive such as the polyacrylates and polyvinylether adhesives. For use in securing biomedical electrodes, a compound such as sodium chloride is also required in order to confer electrical conductivity on the adhesive. A further requirement is that the cohesive force of the adhesive, a measure of its structural integrity, should be greater than its adhesive force so that the electrode can be removed from the substrate without leaving an unacceptable residue.

Although the chemical nature of conducting, pressure-sensitive adhesive coatings for biomedical electrodes is wide, adhesion is lost in all such cases when the substrate and/or the environment is wet. Loss of adhesion in these cases is due to the adhesive absorbing moisture and swelling. Consequently, the electrode becomes detached from the skin surface. In addition, water effectively acts as a lubricant between skin and pressure-sensitive adhesive, preventing full bond strength from being developed and leading to immediate or rapid bond failure. The properties of conventional, pressure-sensitive adhesives known in the art may be found in Satas, D (Editor): Handbook of Pressure-Sen- Technology, Van Nostrand Reinhold, New York, 1982.

Biomedical electrode systems with pressure-sensitive adhesive interfaces are used, for example, in the monitoring of electrical activity of underlying muscles or a heart. In the case of muscles, the resulting signal being recorded is known as an electromyogram; in the case of the heart, the signal is known as an electrocardiogram.

A disadvantage of pressure-sensitive electrode adhesives known in the art is their inability to cope with exposure to significant amounts of moisture. Under very wet conditions adhesion is lost as the adhesive absorbs moisture and swells, with a consequent failure of signal monitoring.

Moisture activated adhesives are known in the art. Such adhesives are presented in the dry state and only exhibit adhesive properties when moistened, for example, paper labels or postage stamps coated with a dried gum. A disadvantage of such wet-stick adhesives is that they must be pre-moistened before being applied to the site of use.

A particular example of a biomedical electrode system which is required to function in a wet environment is an electrode used in the monitoring of human foetal heart rate during labour. The human foetus in the birth canal is surrounded by a considerable volume of aqueous fluid, about one liter. The foetal skin is also lightly coated with a protective material, the vernix. Under these conditions, an electrical sensor cannot be secured to the foetal skin by means of a conventional, pressure-sensitive adhesive. In May and Mahlmeister (1990): Community Maternity Nursing. Nursing Process and the Childbearing Family, 2nd. edn:., Lippincott, Pa., there is disclosed a design for a foetal scalp electrode in which the interface between the foetal skin and the signal conducting substance is made by means of a metal clip secured to the foetal head. The use of such electrodes, which detect the electrical energy produced during each cardiac cycle, is well-known in the art. The design suffers from several disadvantages:

(a) It causes trauma to the foetal skin, which is punctured by the metal clip. The extent of foetal distress caused by this trauma has been widely reported.

(b) Care must be taken during application to ensure that the electrode is placed over the parietal bone of the foetal scalp and not over the anterior or posterior fontanelles.

(c) There is a risk of trauma to such areas of the foetus as the spine, eyes etc. if the electrode is incorrectly applied.

(d) It has been reported in the literature that the sharp metal clip frequently punctures the skin of the person inserting the electrode. This has serious implications if the mother is HIV positive or is a carrier of other transmittable diseases such as hepatitis.

(e) It is comparatively expensive.

Thus, there exists a need for a foetal monitor electrode system which will possess one or more of the following characteristics:

(a) It will give a clear, low noise signal.

(b) It will be disposable, requiring no special preparations to be made before application.

(c) It will have no sharp components.

(d) It will not puncture the foetal skin.

(e) It will not present any risk to attending medical and other staff.

(f) It will attach directly to the foetal skin by an adhesion process.

(g) It will remain reliably attached throughout the period of labour, even in the presence of aqueous fluid.

(h) It will be easy to remove.

(i) It will leave no toxic residue on, or cause any damage to, the foetal skin.

(j) It can be fabricated by conventional mass production techniques known in the art. Consequently, it will be comparatively inexpensive.

(k) It can be attached to a foetal monitor and recording device by conventional means known in the art.

The invention, therefore, provides a biomedical electrode device comprising an electrically insulating substrate, an electrode on the substrate, and a moisture-activated electrically conductive bioadhesive layer on the electrode, the bioadhesive layer having an adhesion of between 50 and 500 g/cm$^2$ and a water content of less than 25% w/w.

In this context, adhesion may be defined as the state in which two bodies, in the form of condensed phases, are held together for extended periods by interfacial forces. These forces may involve covalent bond formation, mechanical, chemical or physical interactions. When one or both adherents are of a biological nature the process is known as bioadhesion. Of particular significance is Type III bioadhesion in which artificial material is made to adhere to a biological substrate. Bioadhesion is a relatively new area of study. Since there is no overall accepted theory of bioadhesion, the development of bioadhesives has tended to be empirical. In many cases adhesion is to epithelium coated with a thin gel layer of mucus. Mucins, viscoelastic glycoproteins, constitute the main components of mucus. Adhesion to this mucosal gel layer is referred to as mucoadhesion. Therefore, viscoelastic polymer formulations for use as bioadhesives have to be tailored to the nature of the biological substrate.

The surface of a biological substrate carries a negative charge. Therefore, polycations present the best opportunity for successfully formulating bioadhesives. However, these tend to disrupt cell membranes when used in isolation, raising the important issue of adhesive biocompatibility. For this reason bioadhesive hydrogels are preferred. Hydrogels are cross-linked hydrophilic molecules, either synthetic or naturally occurring, which have the ability to swell in water without dissolving, and to retain water within their structure. These properties confer a high degree of biocompatibility on hydrogel polymers, hence their extensive applications in medicine. Therefore, in one particular embodiment of the invention, the bioadhesive, moisture-activated electrically-conducting interface is formed from one or more hydrogels, together with the addition of a conducting material known in the art, typically an ionic salt, and with the further addition, where necessary, of a plasticising agent capable of rendering the dried interface pliant and conformable. If the bioadhesive formulation possesses sufficient inherent electrical conductivity, the salt component may be omitted.

BRIEF DESCRIPTION OF THE DRAWINGS

The invention will be understood in greater detail from the following description of preferred embodiments thereof given by way of example only and with reference to the accompanying drawings in which:

FIG. 1 is a plan view of a first embodiment of a biomedical electrode device according to the invention;

FIG. 2 is an elevation of the electrode device of FIG. 1 of the drawings;

FIG. 3 is a perspective view of the electrode device of FIG. 1 of the drawings;

FIG. 4 is a plan view of a second embodiment of a biomedical electrode device according to the invention;

FIG. 5 is a cross-sectional view of the electrode device taken along the line V—V of FIG. 4 of the drawings and viewed in the direction of the associated arrows;

FIG. 6 is a plan view of a third embodiment of biomedical electrode device according to the invention;

FIG. 7 is a cross-sectional view of the electrode device taken along the line VII—VII of FIG. 6 of the drawings and viewed in the direction of the associated arrows;

FIG. 8 is a perspective view of the electrode device of FIG. 6 of the drawings; and FIGS. 9 to 12, 13a, 13b, 14a, and 14b are cross-sectional views of further embodiments of electrode devices according to the invention, FIG. 15 demonstrates the in vitro adhesion properties of 10% w/w Gantrez AN 139 films containing variable amounts of glycerol as plasticizer with respect to initial adhesion and on first and second restick. All points represent the mean ±SD adhesion results for nine replicates. All tests were carried out using wet hairy piglet skin.

In the Figures the same or equivalent parts are given the same reference numerals.

DETAILED DESCRIPTION OF THE PREFERRED EMBODIMENT

Figure 15:
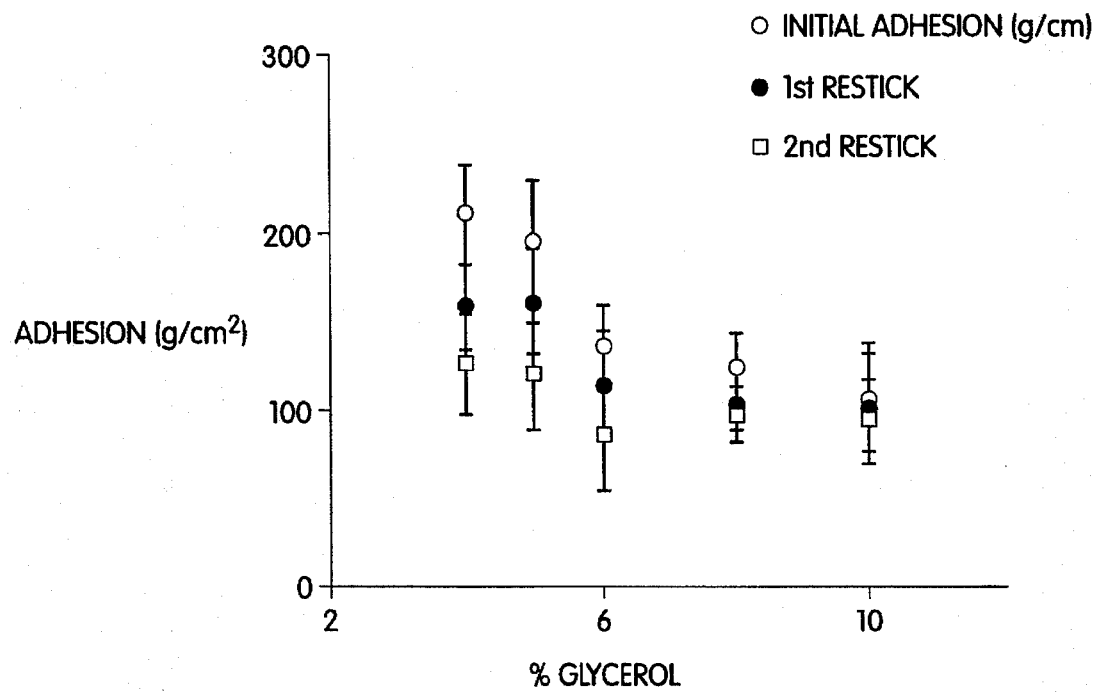
Figure 16:
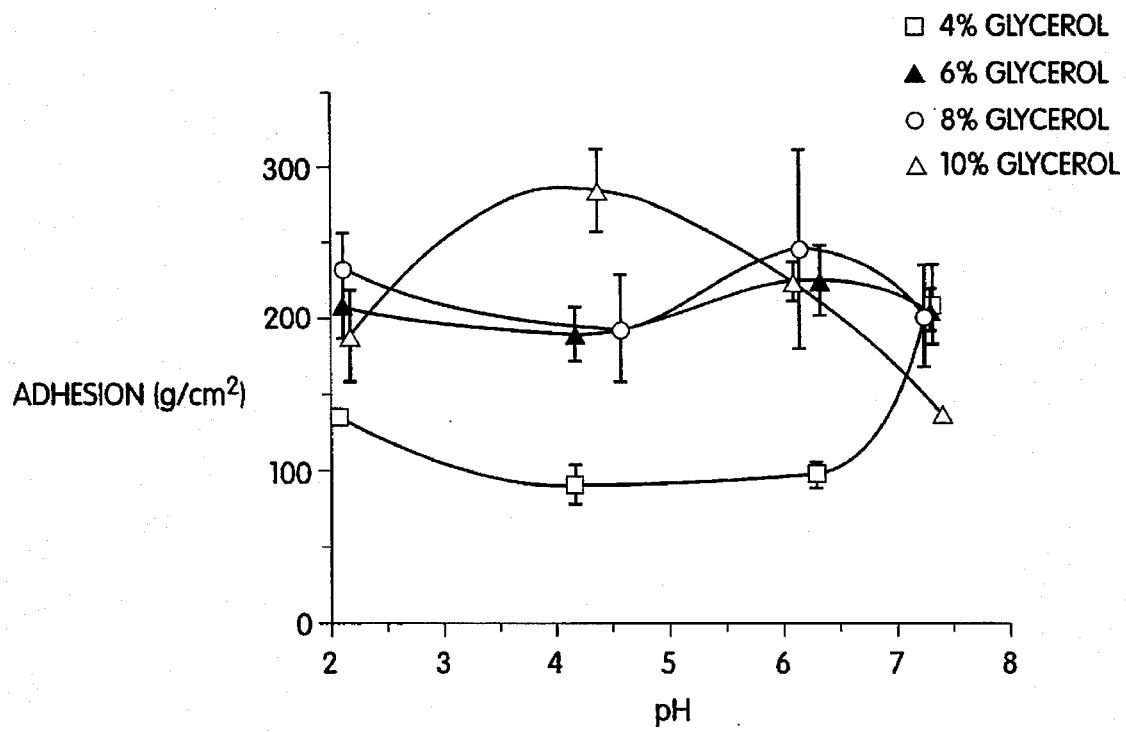
FIG. 16 demonstrates pH-adhesion relationships for 10% w/w Gantrez AN 139 in water with varying amounts of glycerol added.
Figure 17:
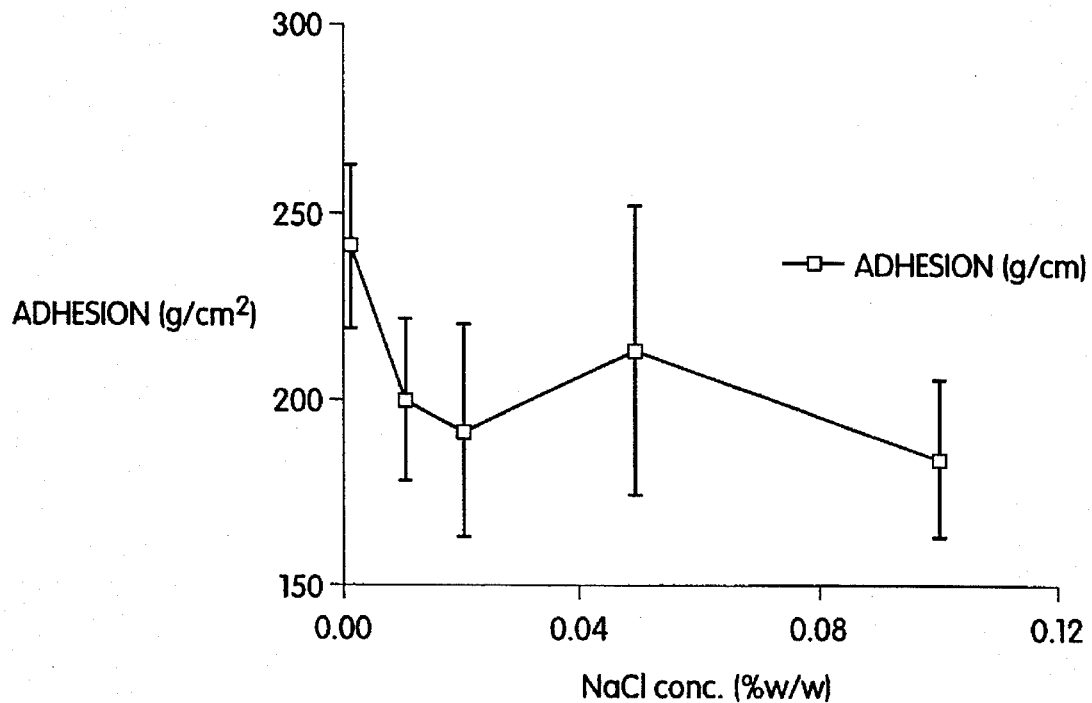
FIG. 17 demonstrates the effect of salt concentration on adhesion in respect of 10% w/w Gantrez AN 139, 5% w/w glycerol and pH adjusted to 5.3±0.18 with concentrated NaOH. Error bars represent the SD of the mean for six replicates.
Figure 18:
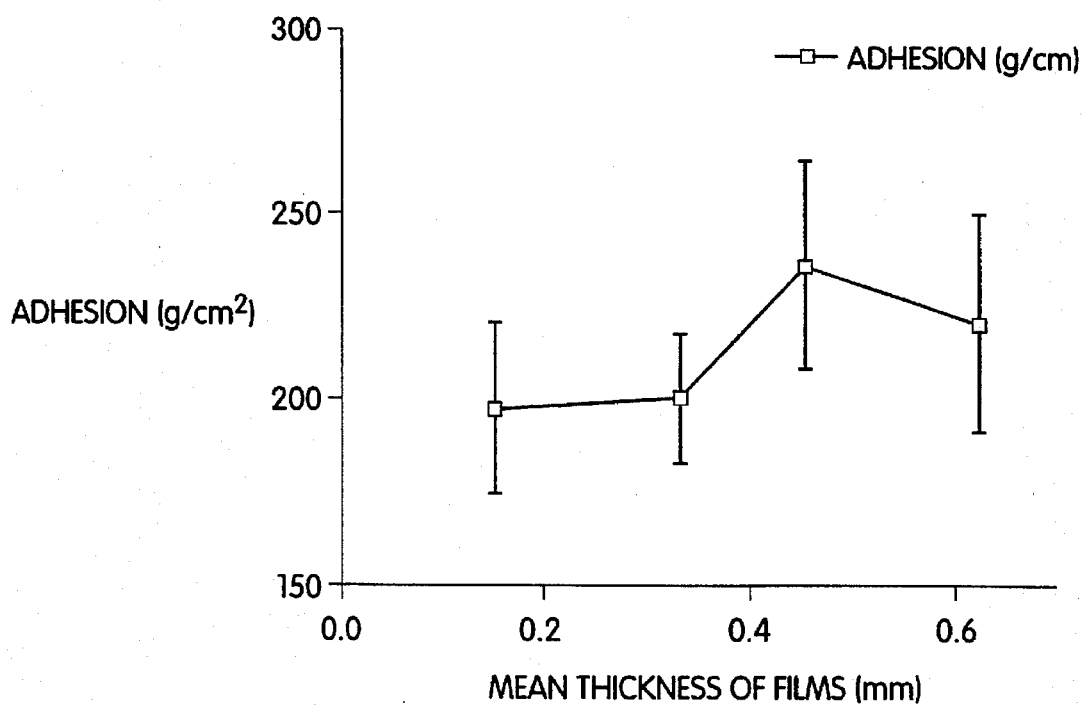
FIG. 18 demonstrates the effect of thickness of film on adhesion in respect of 10% w/w Gantrez AN 139, 5% w/w glycerol and pH adjusted to 5.3±0.18 with concentrated NaOH. Error bars represent the SD of the mean for nine replicates. The mean thickness values were obtained from ten replicates.

Referring now to the drawings and in particular to FIGS. 1–3 thereof, there is shown an electrode device 10 according to the invention which comprises a relatively thin electrically insulating substrate 11 having an obverse side 21; a reverse side 22; a proximal end 23; and a distal end 24.

A foetal electrode sensor 12 and associated lead 13 is deposited onto the obverse side 21 of the substrate 11 at the proximal end 23 thereof. A reference or indifferent electrode sensor 14 and associated lead 15 is deposited onto the reverse side 22 of the substrate 11 also at the proximal end 23 thereof. Thus, the foetal electrode sensor 12 and the reference electrode sensor 14 are in substantially parallel spaced apart relationship. A means of making electrical connection to each of the two leads 13, 15 is provided by extending the leads 13, 15 from the proximal end 23 to the distal end 24. An insulating layer 16 is deposited over the foetal electrode lead 13 so as to leave the sensor 12 and the free end of the lead 13 located at the distal end 24 exposed, the latter being necessary for making electrical connection to a monitoring device (not shown). The lead 15 from the sensor 14 may also be covered by an insulating layer. This is not essential as the sensor 14 and the lead 15 may both serve to make electrical contact with surrounding fluids etc. of the environment in which the electrode device 10 will be used.

Having regard to the fact that the electrode device 10 will be for monitoring a foetus before or during delivery, the electrode device 10 should preferably be relatively thin, lightweight and flexible in order to minimise the strength of adhesion required; to maximise electrical contact; to minimise or avoid trauma to the foetal head; and to minimise or avoid discomfort to the mother both during electrode application and the delivery process itself. Those skilled in the art will recognise that a number of widely available materials meet the requirements for the substrate 11. A particularly preferred embodiment of the present invention uses as the substrate 11 a non-woven polyester sold under the trade name "Melinex" and available in a range of film thicknesses. However, the invention is not limited in its scope by the use of any given substrate material which meets the necessary design requirements.

The sensors 12, 14 and the leads 13, 15 may be deposited by, for example, screenprinting thin layers of conducting serographic ink onto a suitable polyester or polycarbonate substrate 11. Suitable inks include those optimally loaded with either silver or a combination of silver and silver chloride particles. The sensors 12, 14 may be printed or otherwise deposited using a different ink to that used to print or deposit their connecting leads 13, 15. Inks loaded with silver and silver chloride particles are found to be suitable for the sensors 12, 14 as they give rise to good electrode-tissue interface electrical characteristics. Silver-loaded inks, on the other hand, give rise to layers with high conductivity characteristics and hence are suitable for depositing connecting leads 13, 15.

It is preferable that the connecting leads 13, 15 make contact centrally with the electrode sensors 12, 14. To achieve this, a pair of circularly shaped openings 25, 26 is provided in the substrate 11 at the proximal end 23. Contiguous with the opening 25 and in parallel spaced apart relationship relative to the leads 13, 15 is a slit 27; similarly, a slit 28 is provided which is contiguous with the opening 26. As will be observed from FIG. 3, the provision of the holes 25, 26 and associated respective slits 27, 28 enables the leads 13, 15 to move in the direction of the arrows 29 relative to the proximal end 23 of the electrode device 10.

The foetal electrode sensor 12 is coated with a film-forming layer 17. The layer 17 on drying is non-adherent on dry surfaces, contrary to the conventional pressure-sensitive adhesives. It is, therefor, readily handled and has excellent storage properties. The layer 17 is activated by moisture when the electrode 10 is offered to a moist surface, such as a foetal scalp. It does not, therefore, require a pre-moistening step. A further advantage of the layer 17 is its ability to maintain sufficient strength of adhesion to secure the electrode device 10 to a surface such as the foetal scalp, even in the presence of a substantial amount of aqueous fluid. In these respects, the invention differs from known wet-stick adhesives.

The film-forming layer 17 may be prepared using a bioadhesive gel or viscous solution by conventional means known in the art and drying to a low water content, drying being complete when all tack is lost from the resulting dried film. Thus, the layer 17 may be made from polymeric components in an aqueous base and at a total polymer concentration by weight in the wet state of between 0.01% and 50%, but preferably between 1 and 20% by weight of the total mixture, suitable polymers including polyvinylpyrrolidone, polyvinylal—cohols. carbomers, cellulose derivatives such as methyl cellulose and sodium carboxymethylcellulose, hydroxyalkyl celluloses such as hydroxyethylcellulose, hydroxypropylcellulose and hydroxypropylmethylcellulose. polyoxyethylene polyoxypropylene diol block copolymers. poly (methyl vinyl ether/maleic anhydride) copolymers. vinylpyrrolidone copolymers such as vinylpyrrolidone/vinyl acetate copolymers, methacrylate film-forming derivatives sold under the trade name Eudragit.

Suitable plasticisers for incorporation into the layer 17 at a total plasticiser concentration by a weight of between 0.25% and 30%, but preferably between 2 and 25% by weight of the total mixture include dimethyl phthalate, diethyl phthalate, dioctyl phthalate. glycerin, polyols such as ethylene glycol, diethylene glycol, triethylene glycol, polethethylene glycol, propylene glycol, sorbitol and glycerol, nonylphenol—ethylene oxide adducts sold under the trade name Antarox, ethyl glycolate and ethyl sulphonamide derivatives sold under the trade name Santicizer, tricresyl phosphate, dimethylsebacate, ethyl glycolate.

Suitable electrically conducting salts for enabling the layer 17 to be electrically conductive and which may be added to the polymeric components include at a total concentration by weight of between 0% and 10% but preferably between 0.01% and 0.25% by weight of the total mixture sodium chloride, potassium chloride, potassium dihydrogen phosphate, dipotassium hydrogen phosphate, potassium citrate. Electrical conduction may also be achieved by addition of alkali or acid to the polymeric components.

In a preferred embodiment of the present invention, the polymeric component is a poly (methyl vinyl ether/maleic anhydride) copolymer sold under the trade names Gantrez AN, Gantrez S and Gantrez ES. In a particularly preferred embodiment, the polymeric component is Gantrez AN 139 or Gantrez AN 139 in combination with polyvinylpyrrolidone.

A further preferred embodiment of the invention provides for the addition to Gantrez AN 139 aqueous solution or Gantrez AN 139/polyvinylpyrrolidone aqueous solution of glycerol as a plasticiser and sodium chloride as an enhancer of electrical conduction. Glycerol is present in a final concentration in the aqueous solution, before drying, of between 1 and 40% w/w, preferably 5% w/w and sodium chloride is present in a final concentration in the aqueous solution, before drying, of between 0.001 and 5% w/w, preferably 0.1% w/w.

The following examples are preferred formulations for the layer 17. Those skilled in the art will understand that these formulations are disclosed by way of example and nothing that is stated herein shall be taken to restrict the scope of the invention to those specific materials mentioned.

EXAMPLE 1

| | |
|---|---|
| Gantrez AN 139 | 10% w/w |
| Glycerol | 5% w/w |
| Sodium Chloride | 0.1% w/w |
| Concentrated Sodium Hydroxide sufficient to adjust pH of final solution to 5 | |
| Water | q.s. |

EXAMPLE 2

| | |
|---|---|
| Gantrez AN 139 | 15% w/w |
| Glycerol | 7.5% w/w |
| Kollidon 90 | 5% w/w |
| Sodium Chloride | 0.1% w/w |
| Concentrated Sodium Hydroxide sufficient to adjust pH of final solution to 5 | |
| Water | q.s. |

The solutions are formed by conventional means known in the art, using slow stirring at room temperature. The resulting solutions are relatively viscous. Entrained air bubbles may be removed by subjecting the solutions to degassing under vacuum, preferably overnight, or by centrifuging the solutions, for example, at 4000 r.p.m. for 20 minutes.

The layer may be formed by casting the polymer solution such as is disclosed in Example 1 or Example 2 below, directly onto a head 20 of the electrode device 10 and drying to remove water, thus forming a pliable, non-tacky, non-adhesive, film. The head 20 of the electrode device 10 is that part of the device 10 containing the sensors 12, 14 and the proximal ends of the leads 13, 15. Casting may be done by conventional means known in the art, including the use of a casting knife with a variable aperture. Alternatively, the layer 17 may be directly deposited, using a suitable template, onto the head 20. Drying may be achieved by conventional means known in the art, including use of a tray drier, vacuum oven or tunnel dryer. Drying may be carried out at temperatures between ambient and 150° C., preferably 60° C. The drying time varies depending on the solution formulation and the type of drying process used. The water content of the final, dried film is preferably less than 25% w/w.

The adhesion properties of electrode 10 have been determined in vitro using neonate, hairy porcine skin as a model. The test method is known in the art and described in Woolfson, A. D et al. International Journal of Pharmaceutics, volume 84, pages 69–76 (1992). With respect to the adhesion properties of the electrode 10, variables studied included the effect on adhesion of plasticiser concentration, pH, salt concentration and thickness of deposited film. Results of the in vitro experiments are shown in FIGS. 16–19. A particular feature of the conducting bioadhesive wet-stick interface is its ability to allow removal and subsequent repositioning/replacement of the electrode, with adherence characteristics maintained. This is demonstrated by the results shown in FIG. 15.

The ability of the electrode 10 to persist in adhering to skin was studied by adhering it to neonate porcine skin and immersing the whole in one liter of phosphate-buffered saline at 37° C. Persistence of adherence was determined visually by removal and inspection of the test samples at 15 minute intervals. Testing was discontinued after 6 hours, at which time the electrode 10 remained firmly adhered to the porcine skin substrate.

Figure 19:
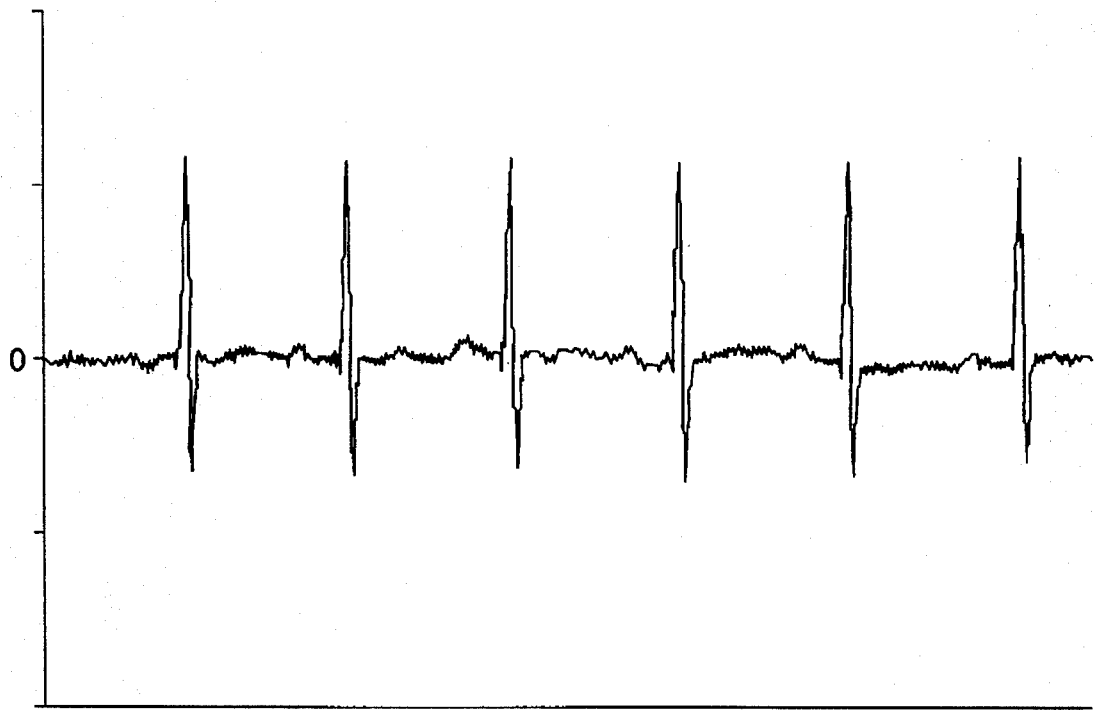
FIG. 19 is a trace of foetal heart using the electrode device according to the invention.

The electrode 10 was tested in vivo for adherence to foetal skin and quality of electrical signals obtained. The electrode 10 adhered immediately to unwashed or otherwise pretreated foetal skin and remained firmly attached throughout the duration of the assessment. A sample of the trace obtained is shown in FIG. 19.

In FIGS. 4 and 5 of the drawings, there is shown a second embodiment of an electrode device 100 according to the invention which is similar in many respects to the electrode device 10 and like numerals for equivalent components are used in the drawings. It will be recognised that FIG. 4 shows a "blank" from which the device will ultimately be formed by trimming surplus substrate material from around the electrodes and leads. [For reasons of clarity, the insulating layer 16 and the film-forming layer 17 are omitted from FIG. 4 of the drawing.] In addition, the composition of the layer 17 is similar to that described with reference to the electrode device 10. The essential differences between the electrode device 100 when compared with the electrode device 10 are as follows. Whereas the electrode device 10 has the electrode device sensors 12, 14 located on the obverse side 21 and the reverse side 22 respectively both electrodes 12, 14 of the electrode 100 are located on the same side of the substrate i.e. either the obverse side 21 or the reverse side 22. However, the electrode sensors 12, 14 are in linear relationship so that the reference electrode sensor 14 is located at the extreme proximal end 23 of the substrate 11 with the foetal electrode sensor 12 located albeit at the proximal end 23 but in the direction of the distal end 24 of the electrode 100. The respective associated leads 13 and 15 are also located on the same side of the substrate 11 as the sensors 12, 14 but to enable the lead 15 to be electrically isolated from the lead 13, the lead 15 has a curved path or portion 15a which circumlocates the sensor 12. Located between the sensor 12 and the sensor 14 is a fold line 101 so that part of the substrate 11 containing the sensor 14 may be folded in the direction of the arrows 103 between 100° and 160° as shown in FIG. 5 of the drawings. The relative positions of the sensors 12, 14 will now be clearly seen in FIG. 5 of the drawings being at an angle of between 20° and 80°. If desired, a pair of side walls 102 may connect the sides of the curved part of the substrate 11 with the linear part of the substrate 11 to form a housing which constitutes a finger cradle 104. The side walls 102 may be formed from laterally extending flaps of the substrate material which are left attached to the device on either side of the electrodes after trimming the blank as referred to above, or they may separate pieces which are individually attached. The provision of the cradle 104 enables the electrode 100 device to be positioned relatively easily by the insertion of, for example, an index finger into the cradle 104, so as to carry the electrode device 100 to the site of use, e.g. the head or scalp of the baby being delivered and placement of the electrode 100 by the application of suitable pressure so that the layer 17 and hence the foetal electrode sensor 12 is in contact with the head of a baby with relatively long leads trailing along the leg of the mother to which they may be taped by conventional means. The leads 13, 15 can then easily be connected to suitable monitoring equipment.

Figures of the drawings 6–8 show a third embodiment of an electrode device 200 according to the invention which is substantially similar to the electrode device 100 except as follows. [For reasons of clarity the insulating layer 16 and the film-forming layer 17 are omitted from FIG. 6 of the drawings.] Whereas the leads 13, 15 of the electrode device 100 are on the same side of the substrate 11, in the electrode device 200, the lead 13 is on the same or obverse side 21 of the substrate 11 as the sensors 12, 14 and the lead 15 is on the reverse side 22 of the substrate 11. This arrangement allows for a relatively simpler construction of electrode device 200 in that the curve path 15a is not required. To enable electrical contact to be made between the lead 15 and the sensor 14, an opening 201 is provided centrally in the sensor 14 so that electrical connection may be made by the provision of, for example, electrically conductive ink in the opening in electrical contact with the sensor 14 and the lead 15.

FIG. 9 of the drawings shows a fourth embodiment of an electrode device 300 according to the invention which is substantially similar to the device 10 except as follows. The proximal end 23 of the substrate 11 has attached thereto by suitable means a piece of substrate material 11a which projects towards the distal end 24 of the substrate 11. A pair of side walls 102 connects the material 11a with the substrate 11 to form, in a manner similar to that described with respect to FIGS. 4–5 of the drawings, a finger cradle 104.

In FIG. 10 of the drawings, there is shown a fifth embodiment of an electrode device 400 according to the invention which is substantially similar to the electrode device 100 of FIG. 5 except as follows. Instead of providing a single curve of between 100° and 160°, a double curve is employed so that the reference electrode 14 is in substantially parallel spaced apart relationship relative to the electrode 12 having been moved through an angle of about 180°.

Since the foetus lies in a bath of amniotic fluid that contains ions and is thus conductive, the use of surface electrodes can result in an inadequate ECG trace due to electrical shorting between electrodes. This can be mitigated by surrounding the adhesive 17 and sensor 12 with an annulus or band of insulating material.

Embodiments of such a design are shown in FIGS. 11 and 12. In FIG. 11 the band of insulating material 50 extends to the edges of the substrate 11, whereas in FIG. 12, the band of insulating material is itself surrounded by a further band of moisture activated bioadhesive material 51. The bioadesive material 51 ensures firm mechanical contact between the insulation material 50 and the foetal scalp, and even firmer contact can be achieved by making the thickness of the outer bioadhesive layer 51 less than that of the insulation material 50. The outer layer 51 may be less conductive than the main bioadhesive layer 17. In the case of both FIG. 11 and FIG. 12 it is preferable that the insulating material 50 be made of a material substantially more rigid than the bioadhesive layer so that the band 50 can penetrate the vernix coating to make firm contact with the foetal scalp, yet not so rigid that it cannot deform to conform with body contours without traumatizing the foetal skin. Further, although only a single band 50 of insulating material has been shown in FIGS. 11 and 12, there may be more than one band arranged concentrically within one another. In such a case the multiple bands may be the same or different composition and may be located immediately adjacent one another or separated by intermediate regions of bioadhesive.

A further embodiment of the invention is shown in FIGS. 13A and 13B. In this case the substrate 11 is formed or moulded, along with the electrodes 12 and 14 and the insulating layer 16, to form a cup-shaped housing containing the bioadhesive material 17. This avoids the need for a surrounding band of insulation 50 as described above. Applying the device using moderate pressure, as shown in FIG. 13A, will ensure that the "rim" or edge of the cup 11', which is substantially more rigid than the bioadhesive layer 17, penetrates the vernix covering to make firm mechanical contact with the foetal scalp. This will greatly reduce the possibility of electrical shorting between the two electrodes 12 and 14. Applying sufficient pressure to the device to cause an indentation in the cup-like housing 11' will give rise, upon release, FIG. 13B, to a suction force which will help to ensure that the firm mechanical contact is maintained and reduce further the possibility of electrical shorting between the electrodes 12 and 14

Alternatively, FIG. 14A and 14B, suction may be applied to the interior of the cup 11' by using a vacuum pump, a suction "bulb" or a syringe, for example. One end 53 of a suction tube 52 is inserted through a self-sealing membrane 54 in the cup 11', FIG. 14A, and its other end is attached to the vacuum pump or other suction device. Once the device has been firmly attached, the suction tube 52 can be withdrawn, FIG. 14B.

Of course, a finger cradle can be provided in the case of the embodiments of FIGS. 11 to 14. However, these are not shown in order to avoid overcomplicating the Figures. As an alternative to a finger cradle, in all embodiments of the invention described above, one can provide a slot in the substrate 11 for engagement by an external applicator.

In the electrode devices hereinbefore described a release liner (not shown) may be provided which forms a protective layer over the obverse side of the electrode device and which is removable immediately prior to use.

The electrode device according to the invention may also be used for transcutaneous electrical nerve stimulation for the treatment of, for example, urinary incontinence, or for electrodental anaesthesia or as referred to above, for the electrical monitoring of a foetal heart.

The invention is not limited by or to the specific embodiments described which can undergo considerable variation without departing from the scope of the invention.

We claim:

1. A biomedical electrode device comprising an electrically insulating substrate, a first electrode on the substrate, the first electrode having thereon a non-tacky moisture-activated electrically conductive bioadhesive layer which has a water content of less than 25% w/w and which is activated without pre-moistening when offered to moist fetal skin to adhere to such skin with an adhesion of between 50 and 500 g/cm$^2$, and a further electrode on the substrate at a position to serve as a nonskin contacting reference electrode, the substrate further having first and further electrically conductive leads thereon respectively connected to the first and further electrodes.

2. A device as claimed in claim 1, wherein the bioadhesive layer comprises a polymer or mixture of polymers.

3. A device as claimed in claim 2, wherein the polymer or mixture of polymers comprises a poly (methyl vinyl ether/maleic anhydride) copolymer.

4. A device as claimed in claim 3, wherein the polymer or mixture of polymers further comprises polyvinylpyrrolidone.

5. A device as claimed in claim 2, wherein the bioadhesive layer further comprises a conducting material and a plasticizing agent.

6. A device as claimed in claim 1, wherein the further electrode is on the opposite side of the substrate to the first electrode.

7. A device as claimed in claim 6, wherein one or more bands of insulating material surrounds the bioadhesive layer, the insulating material being substantially more rigid than the bioadhesive layer.

8. A device as claimed in claim 7, wherein a further bioadhesive layer surrounds the band of insulating material.

9. A device as claimed in claim 6, wherein in the region of the electrodes the substrate is cup-shaped with the first electrode formed on the inside of the cup and the further electrode formed on the outside of the cup, the bioadhesive layer being formed inside the cup and the edges of the cup being substantially more rigid than the bioadhesive layer.

10. A device as claimed in claim 1, wherein the further electrode is on the same side of the substrate as the first electrode, the substrate being folded or foldable between the first and further electrodes so that the portion of the substrate bearing the further electrode is or can be folded back to maintain the further electrode out of contact with a surface with which the first electrode is in contact.

11. A device as claimed in claim 10, wherein the first and further electrically conductive leads are on opposite sides of the substrate, and one of the leads makes contact with the respective electrode through an aperture in the substrate.

12. A device as claimed in claim 1, wherein the first lead is connected to a center region of the first electrode at a location separated from an edge region thereof by a pair of slots extending longitudinally on opposite sides of the first lead.

13. A device as claimed in claim 1, wherein the substrate is configured to form a finger cradle or slot for other external applicator to facilitate placement of the device.

* * * * *